United States Patent [19]

Beiser

[11] Patent Number: 4,822,343
[45] Date of Patent: Apr. 18, 1989

[54] BLOOD COLLECTION DEVICE WITH EJECTABLE TIPS

[76] Inventor: Louise Beiser, 18585 W. Spring Lake Rd., Spring Lake, Mich. 49456

[21] Appl. No.: 98,989

[22] Filed: Sep. 21, 1987

[51] Int. Cl.[4] ............................................. A61M 5/00
[52] U.S. Cl. .................................... 604/187; 604/243; 128/763
[58] Field of Search ............... 604/187, 242, 243, 240, 604/241; 128/763, 764, 765

[56] References Cited

U.S. PATENT DOCUMENTS

| 2,806,473 | 9/1957 | Lingley | 604/243 |
|---|---|---|---|
| 2,875,760 | 3/1959 | Haber | 604/242 |
| 3,434,468 | 3/1969 | Barr, Sr. et al. | 604/243 |

FOREIGN PATENT DOCUMENTS 883053 7/1953 Fed. Rep. of Germany ...... 604/187

Primary Examiner—John D. Yasko
Attorney, Agent, or Firm—Waters, Morse & Harrington

[57] ABSTRACT

A blood collecting device for use in collecting blood samples. A blood collecting device comprises a tubular holder, needle assembly and tube where the needle assembly is engageably retained to the holder by a latching means. The latching means may be manually disengaged allowing the needle assembly to be ejected affirmatively by a spring loaded ejection means without touching the needle manually.

7 Claims, 2 Drawing Sheets

BLOOD COLLECTION DEVICE WITH EJECTABLE TIPS

BACKGROUND OF THE INVENTION

The practice of modern medical technology has adopted the usage of a standard device or method for the collection of blood samples from patients. Although the blood collection devices may be made by a number of different companies, they share the same basic characteristics. The typical unit comprises a tubular holder, preferably of plastic construction, wherein one end terminates in a tapered projection known as a needle mount. The other end has an opening of a size that is compatible with the receipt of the tubes used in the blood collecting process.

Specifically, the needle mount is made to receive a double ended needle assembly that has a hub disposed about the central portion of the needle. The hub is compatibly sized to mate with the end of needle mount and be retained thereon. Once assembled in this manner, one end of the double ended needle extends inwardly into the holder and the opposite end of the needle extends outwardly from the hub.

A number of different needle fittings are known. These differ primarily by the methods in which they connect to the needle mount. For example, one method is a threaded engagement of the needle fitting to the needle mount. Another is known as a bayonet style, in which both components have spaced flanging that allows the insertion of the needle fitting into a needle mount, and after a partial turn, the needle fitting is connectibly retained to the mount.

Another type of needle fitting commonly employed on syringes is known as a Luer fitting, which comprises a hub with an internal diameter sized for compatible installation over the outer diameter of the needle mount. The fit is tight enough to cause the hub to be retained on the mount and is overcome by twisting the installed parts in order to release the hub from the mount.

Once the collector is assembled with a needle assembly, the usual practice is to insert the needle extending from the collection holder into the patient whose blood is going to be drawn. At the same time, a specially prepared tube is positioned into the opening at the other end of the holder. One end of the tube is closed, and the other end is provided with a puncturable seal that protects the contents of the tube from contamination from the outside environment. The interior of the tube is placed under a slight vacuum. The tube with the sealed end is inserted first and is pushed through the holder until it contacts the inwardly projecting portion of the needle assembly. At the appropriate time, the seal end is punctured by the needle and the vacuum is exposed to the bore of the needle and exerts an extraction force causing blood to be collected into the tube. Once the sample volume has been obtained the tube is withdrawn from the holder, and the holder is withdrawn from the patient. The seal on the tube returns to its sealed state and preserves the integrity of the sample thus drawn. At this point, the tube may be sent for processing.

The holder is designed to be reused while the needle assembly is removed and discarded. One means for removing the needle assembly is a plastic sheath that fits over the outwardly extending portion of the needle assembly and compatibly grips the needle fitting, thereby removing it from the needle mount. In order for the holder to be reused, the above procedure is repeated.

One problem that has been associated with the use of this blood collecting device has been for the tendency of the medical technician to slip while trying to enclose the needle with the plastic sheath after taking a blood sample. This may result at times in the medical technician being punctured by the needle and potentially exposed to the blood of the patient. Of grave concern is the transmission of disease such as hepatitis or AIDS (Acquired Immune Deficiency Syndrome) known to be communicable by such mishaps.

Another problem associated with the standard blood collection assembly is the weakness that develops in the fit between the needle mount and the needle fitting such that separation during the blood sampling process may lead to incomplete collection of the sample, contamination of the sample, and on occasion the separation of the needle fitting from the blood collecting holder with the embarrassing and potentially dangerous situation where the needle assembly remains in the patient.

SUMMARY OF THE INVENTION

In accordance with the present invention, an improved blood collecting device for use in collecting blood samples comprises a tubular holder with an open end and with a needle mount end, where the needle mount end compatibly receives a needle assembly with a hub part with a double-ended needle extending therethrough. The tubular holder receives a vacuum blood collection tube through the open end of the holder. The vacuum tube comprises a substantially cylindrical container closed at one end and having a puncturable seal at the other end. The interior of the tube is evacuated so as to maintain a negative internal pressure. The seal is punctured during insertion by the inwardly projecting portion of the needle extending from the needle assembly mounted onto the collecting device. The assembly is affirmatively retained on the needle mount by a releasable latch situated on the holder in a position to engage the needle assembly. When the latch is released by the user the needle assembly is released from the needle mount with little or no risk of contact with the user.

Additionally, the blood collecting device also comprises the improvement where the needle mount has an ejection means disposed at its base to apply a force to the needle assembly restrained by the latching means. When the latching means is disengaged, the force is sufficient to dislodge the needle assembly from the holder, thereby causing the needle assembly to be directed away from the blood collecting device and towards an appropriate disposal receptacle.

These and other features and advantages of the present invention will become apparent from a description of the preferred embodiment of the present invention set forth below and shown in the appended drawings.

DETAILED DESCRIPTION OF THE PREFERRED EMBODIMENT

Figures 1, 2, 3:
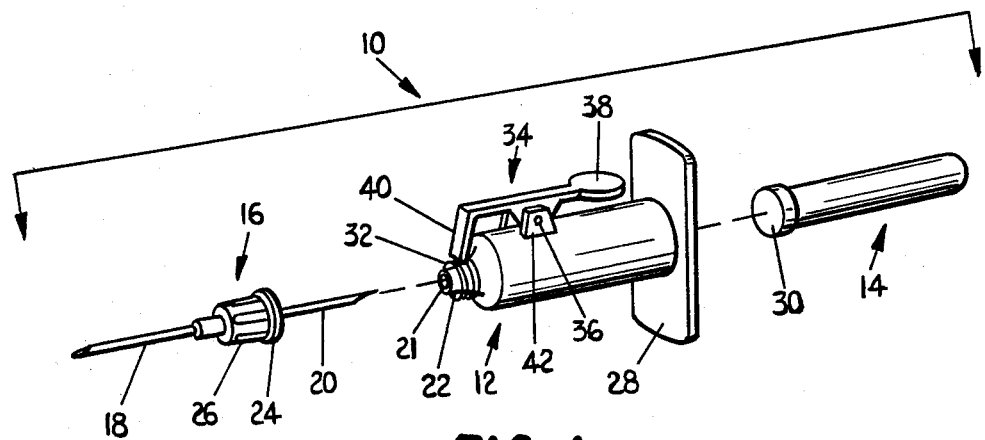
FIG. 1 is an exploded perspective view of the invention on a typical blood collecting device with a Luer type needle fitting.
FIG. 2 is a side cross-sectional view of the tubular holder of the present invention, shown with a latch arm engaging a needle fitting.
FIG. 3 is a side elevational view of the tubular holder of FIG. 2 shown with the latch arm in its disengaged position.

Referring now to the drawings, a blood collecting device 10 is shown in FIG. 1. Collectively, the device comprises three parts, the holder 12, the vacuum blood collection tube 14, and a needle assembly 16 with a Luer type hub fitting 26.

In order to illustrate the function of the three basic components of the blood collecting device, the procedure for sampling is described generally as follows and as in FIGS. 1 and 2. The needle assembly 16 is fixed on the needle mount 22 by guiding the inward needle 20 through the aperture 21 found in the center of the needle mount. Next, the vacuum tube 14 is inserted with the seal end 30 first into the holder 12 through the open end 44. As appropriate, the medical technician will insert the outward needle 18 into the patient, while at approximately the same time beginning to urge the vacuum tube further into the holder barrel 46 and gripping the entire assembly by holder flanges 28. At the point the seal end is punctured by the inward needle 20, the vacuum in the tube will exert an extraction force and cause a blood sample to be withdrawn through the bore of the needle and be collected in the tube. The blood collecting device is then withdrawn from the patient and the tube is withdrawn from the holder barrel. With this general procedure in mind, the improvements exhibited by the present invention will be explained below.

The usage of a Luer type fitting is recommended, although that fitting is not currently in use on blood collecting devices. The present invention relies on similar designs since the engagement of the tip to the device is best accomplished by a slidably removable fitting with a compatible protrusion for latching.

Turning now to FIG. 2, a blood collecting device of the present invention is shown where the needle assembly 16 is affixed to the needle mount 22 while compressing a spring assembly 32. The needle assembly is principally retained to the mount by means of the hub fitting 26 with flange 24. From the drawing, it can be seen that a latch arm 34 with a latch point 40 is contacting the flange of the hub fitting, thereby restraining the needle assembly mechanically.

Figure 4:
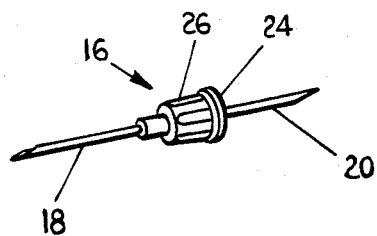
FIG. 4 is a side perspective view of a Luer type needle assembly.

As shown in FIG. 4, a needle assembly with hub fitting 26 has a needle passageway extending through it and defined by outward needle 18 and inward needle 20. Further, the hub fitting has integrally formed flange 24. This hub fitting 26 is known in the medical industry as a Luer type fitting and is one of the more common fittings used on syringes. The embodiments of the present invention relate specifically to the usage of Luer type fittings as opposed to threaded or bayonet mount type fittings. It is recognized however that any needle fittings based on principles similar to that of the Luer fitting would work with the present invention, and to that extent the present invention is not limited to a Luer fitting.

Figure 6:
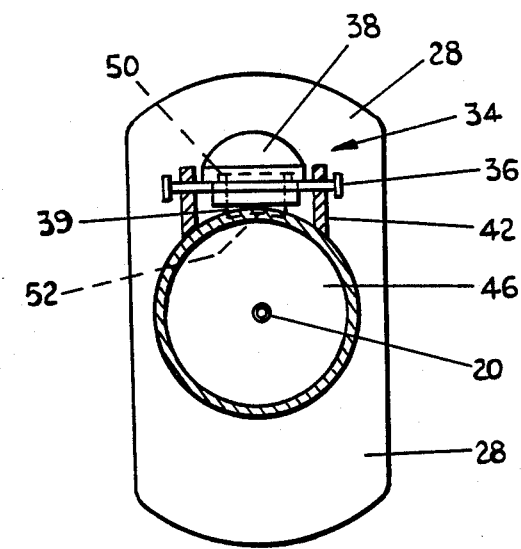
FIG. 6 is a cross-sectional view taken at lines 6—6 of FIG. 5.

The latch arm is allowed to rotate around the pivot pin 36, which is best shown in FIG. 6 as being connected to the latch mounts 42 and through the latch arm. The pivot pin thus acts as an axle in allowing the movement of the latch arm about it. The spring clip 39 is located between the lever end 38 and the body of the holder and continuously exerts a tension on the lever end in a direction that causes the latch point to remain affirmatively contacted against the hub fitting. This force applied to the latch arm as a whole prevents accidental disengagement of the needle assembly from the needle mount. The force can be overcome by manually depressing the lever end, thereby releasing the contact made between the hub fitting and the latch point. The spring clip is constructed from spring steel in the preferred embodiment, although other resilient and flexible materials of construction such as plastic may be utilized. As shown in FIG. 2, the spring clip is installed in and retained by the lever recess 50 and the holder recess 52.

From the above, it can now be understood that the Luer type hub fitting, which is normally retained by the close fit of the hub fitting to the needle mount, is affirmatively engaged by the action of the latch arm on the flange 24. As is shown in FIG. 3, an ejection means of the preferred embodiment is actuated when the latch arm is disengaged by depressing on the lever 38, the needle assembly is then caused to be removed from the needle mount by the urging of the spring assembly 32. This action provides a major benefit in the present invention by eliminating the need for the medical technician to engage the outer portion of the hub fitting of the needle assembly in order to remove it from the blood collecting device after use. The usual practice is to engage the hub fitting with a plastic sheath that ostensibly protects the medical technician from contact with the outward needle 18. In fact, the requisite coordination for successfully inserting the tip of the needle assembly into such a sheath can be beyond the ability of the medical technician at times resulting in the puncturing of the technician's hands or fingers with the tainted outward needle. Precisely for this reason, the object of the present invention is accomplished by allowing affirmative removal of the needle assembly with minimal risks to the medical technician.

Figure 5:
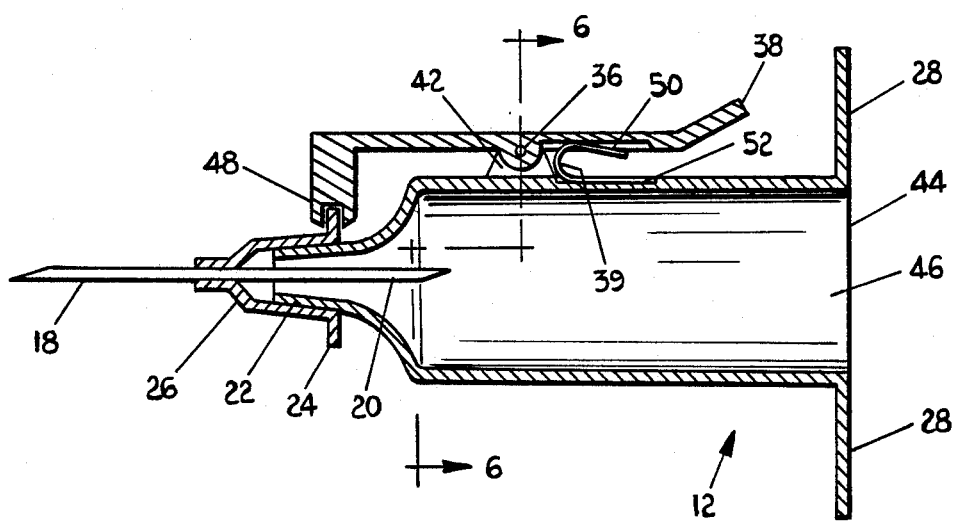
FIG. 5 is a side cross-sectional view second embodiment of the present invention, wherein the holder employs a double tooth latch arm.

A modification of the present embodiment may be seen in FIG. 5 where the contact between the latch arm and the needle assembly is made by means of a double tooth latch point 48. In this embodiment, better control over the position of the needle assembly with a latch arm can be had. It is possible with this modification to discard the needle assembly without the use of a spring assembly, since the depression of the lever 38 will cause the double tooth latch point to urge the flange of the needle assembly outwardly away from the needle mount. This is caused by the engagement of the flange between the two teeth, such that the rotation of the latch arm results in the direct application of an ejection force to the flange. Thus the needle assembly in this instance is ejectable by means of manual and gravitational effort.

From the above, it can be seen that the latch arm can be employed as a lever working through an axle mounted on the side of the holder. The latching of the needle assembly to the holder may also be accomplished by other retaining means, such as a slidable arm. The usage of a latch arm with a pivot pin is illustrative of the practice of the preferred embodiment and in no way represents a limitation on the number, type, or point of placement of other latching devices utilizing the flange of the Luer type hub fitting.

Additionally, the spring clip may be modified so long as a biased tension is applied towards the point of contact of the latch point with the needle assembly. As can be understood, the placement of the spring clip in the preferred embodiment can be altered slightly or springs with reverse tension and anchoring may be employed on the other side of the pivot pin. Other means for applying biased tension about a lever arm are known to those skilled in the art, the selection of which remains an engineering choice in the present invention.

It should be understood that the foregoing represents merely a preferred embodiment of the present invention and that various modifications and changes may be made in the details of construction and operation of the present invention without departing from the spirit and scope of the present invention, as defined in the appended claims.

The embodiments of the invention in which an exclusive property or privilege is claimed are defined as the following:

1. In a blood collecting device for use in collecting blood samples wherein the collecting device comprises a tubular holder with an open end and a needle mount end and a needle assembly having a hub fitting and a double ended needle extending therethrough, the needle assembly being mounted on the tubular holder by inserting one end of the needle through an opening in the needle mount end and sliding the needle longitudinally inward until there is engagement between the hub fitting and the needle mount end, the tubular holder compatibly receiving a blood collection tube through the open end of said holder so as to engage the inwardly extending end of the needle, the improvement wherein the needle mount end and hub fitting comprise mating inwardly tapered surfaces that provide a sealed engagement therebetween when the hub fitting is seated on the needle mount end, the sealing engagement being broken as soon as the hub fitting is moved away from its seated position on the needle mount end, the device comprising manually releasable latch means for affirmatively retaining the hub fitting of the needle assembly seated on the needle mount end, the needle assembly being slidably longitudinally out of engagement with the needle mount end when the latch means is released, the device further comprising automatic, non-manual ejection means for dislodging the needle assembly longitudinally from the needle mount when the latching means is disengaged, the needle assembly moving freely off the end of the needle mount end as soon as the hub fitting is dislodged from its seated position, due to the tapered shape of the needle mount end and the hub fitting.

2. A blood collecting device as in claim 1 wherein the ejection means is a compressible spring positioned between the hub fitting of the needle assembly and needle mount end such that the spring is compressed as the hub fitting is moved into latching engagement with the needle mount.

3. A blood collection device as in claim 1 wherein the latching means comprises a latch member mounted on the tubular holder for movement between a latching position, wherein the latch member engages a cooperating surface on the hub fitting and restrains the hub fitting from longitudinal withdrawal from the needle mount, and a released position, wherein the latch member is disengaged from the needle assembly and the assembly is removed from the needle mount end by longitudinal slidable movement.

4. A blood collection device according to claim 3 wherein the hub fitting has an outwardly extending flange that engages the latch member, the latch member being pivotably mounted on the tubular holder at a point between the ends, a latch point end of the latch member being positioned for retaining engagement with the flange when the latch member is in its latching position, the latch point end moving out of position for retaining engagement with the flange when the latch member is pivoted to the released position, the latch member having a lever end positioned adjacent the tubular holder, the lever end being manually movable to move the latch member to the released position.

5. A blood collection device according to claim 4 wherein the tubular holder includes an elongated tubular body and the needle mount end comprises a tapered projection of reduced diameter on one end of the body, with the projection having the opening therethrough for the needle, the hub fitting positioned longitudinally over the projection and being urged to be retained on the projection in the absence of the latching means only by frictional engagement between the hub fitting and the projection, the latching member comprising an L-shaped member including a first arm extending along the outer surface of the tubular member toward the open end and a second arm connected at substantially right angles to the first arm at the outer end thereof and extending radially inwardly to a position behind the flange on the hub fitting, the latching member being movable between its latching and released positions by manipulation of the first arm of the latching member, the latching member being resiliently biased toward its latching position, the latching member further including cam means for engaging the hub fitting as it is mounted on the projection and moving the latching member to its released position until the hub fitting is mounted on the projection.

6. A blood collection device according to claim 1 wherein the latch means resiliently urges the hub fitting to remain in seated, sealing engagement with the needle mount end until the latch means is released.

7. In a blood collecting device for use in collecting blood samples wherein the collecting device comprises a tubular holder with an open end and a needle mount end and a needle assembly having a hub fitting and a double ended needle extending therethrough, the needle assembly being mounted on the tubular holder by inserting one end of the needle through an opening in the needle mount end and sliding the needle longitudinally inward until there is engagement between the hub fitting and the needle mount end, the tubular holder compatibly receiving a blood collection tube through the open end of said holder so as to engage the inwardly extending end of the needle, the improvement wherein the device comprises manually releasable latch means for affirmatively retaining the needle assembly on the needle mount end, the needle assembly being slidable longitudinally out of engagement with the needle mount end when the latch means is released, the hub fitting having an outwardly extending flange that engages the latch member, the latch member being pivotably mounted on the tubular holder at a point between the ends, a latch point end of the latch member being positioned for retaining engagement with the flange when the latch member is in its latching position, the latch point end moving out of position for retaining engagement with the flange when the latch member is pivoted to the released position, the latch member having a lever end positioned adjacent the tubular holder, the lever end being manually movable to move the latch member to the released position, the outer end of the latch member comprising a double tooth latch point that compatibly retains the flange of the needle assembly until said latch member is manually released to cause release of the needle assembly from the needle mount end of said collecting device.

* * * * *